(12) United States Patent
Schaefer et al.

(10) Patent No.: US 9,672,651 B2
(45) Date of Patent: Jun. 6, 2017

(54) FOUR-DIMENSIONAL RECONSTRUCTION OF REGIONS EXHIBITING MULTIPLE PHASES OF PERIODIC MOTION

(75) Inventors: Dirk Schaefer, Hamburg (DE); Michael Grass, Buchholz in der Nordheide (DE)

(73) Assignee: Koninklijke Philips N.V., Eindhoven (NL)

( * ) Notice: Subject to any disclaimer, the term of this patent is extended or adjusted under 35 U.S.C. 154(b) by 1741 days.

(21) Appl. No.: 12/445,752

(22) PCT Filed: Oct. 10, 2007

(86) PCT No.: PCT/IB2007/054123
§ 371 (c)(1),
(2), (4) Date: Apr. 16, 2009

(87) PCT Pub. No.: WO2008/047268
PCT Pub. Date: Apr. 24, 2008

(65) Prior Publication Data
US 2010/0295846 A1 Nov. 25, 2010

(30) Foreign Application Priority Data
Oct. 17, 2006 (EP) .................................... 06122430

(51) Int. Cl.
*G06T 13/20* (2011.01)
*G06T 11/00* (2006.01)
*A61B 6/02* (2006.01)
*A61B 6/00* (2006.01)
*A61B 8/13* (2006.01)

(52) U.S. Cl.
CPC ............ *G06T 13/20* (2013.01); *G06T 11/006* (2013.01); *A61B 6/02* (2013.01); *A61B 6/4441* (2013.01);
(Continued)

(58) Field of Classification Search
None
See application file for complete search history.

(56) References Cited

U.S. PATENT DOCUMENTS 6,643,392 B1    11/2003   Vaillant et al.
2004/0125908 A1*  7/2004   Cesmeli et al. ................. 378/4
(Continued)

FOREIGN PATENT DOCUMENTS

EP    1310913 A1    5/2003
WO    2004036502 A1    4/2004
(Continued)

OTHER PUBLICATIONS

Weese et al: "Voxel-Based 2-D/3-D Registration of Fluoroscopy Images and CT Scans for Image-Guided Surgery"; IEEE Transactions on Information Technology in Biomedicine, vol. 1, No. 4, pp. 284-293, Dec. 1997.
(Continued)

*Primary Examiner* — Daniel Hajnik (57) ABSTRACT

A method for four dimensional reconstruction of regions exhibiting multiple phases of periodic motion includes the operation of building one or more 3-D reconstructions using a set of 2-D projections. The method further includes the operation of deriving one or more 3-D model segments from each of the one or more 3-D reconstructions, wherein a plurality of 3-D model segments are formed thereby, and wherein each of the one or more 3-D model segments is derived from a single one of the one or more 3-D model segments. The plurality of derived 3-D model segments forms a 4-D reconstruction of the region of interest.

19 Claims, 4 Drawing Sheets

(52) U.S. Cl.
CPC ............... *A61B 6/503* (2013.01); *A61B 6/504* (2013.01); *A61B 6/541* (2013.01); *A61B 8/13* (2013.01); *G06T 2211/404* (2013.01); *G06T 2211/412* (2013.01)

(56) References Cited

U.S. PATENT DOCUMENTS

| | | | |
|---|---|---|---|
| 2006/0058638 A1 | 3/2006 | Boese et al. | |
| 2006/0133564 A1* | 6/2006 | Langan et al. | 378/8 |
| 2007/0036418 A1* | 2/2007 | Pan et al. | 382/131 |
| 2007/0127809 A1* | 6/2007 | Leach et al. | 382/154 |
| 2007/0167801 A1* | 7/2007 | Webler et al. | 600/459 |

FOREIGN PATENT DOCUMENTS

| | | |
|---|---|---|
| WO | 2004072903 A2 | 8/2004 |
| WO | 2005093662 A1 | 10/2005 |

OTHER PUBLICATIONS

Kaus et al: "Automated Segmentation of the Left Ventricle in Cardiac MRI"; Medical Image Analysis 8 (2004), pp. 245-254.

Cohen, E.: "Evaluation of Abdominal Aortic Aneurysms Using Magnetic Resonance Angiography"; Vascular and International Imaging, Section 7, Downloaded From the Internet Apr. 10, 2006, pp. 227-232.

Kato et al: "Prediction of Impending Rupture in Aneurysms Using 4-D-CTA: Histopathological Verification of a Real-Time Minimally Invasive Tool in Unruptured Aneurysms"; Minimally Invasive Neurosurgy 2004, vol. 47, pp. 131-135.

Hayakawa et al: "CT Angiography With Electrocardiographically Gated Reconstruction for Visualizing Pulsation of Intracranial Aneurysms: Identification of Aneurysmal Protuberance Presumable Associated With Wall Thinning"; American Journal of Neuroradiology, vol. 26, pp. 1366-1369, Jun./Jul. 2005.

* cited by examiner

FIG. 1

$\Sigma$ = 4-D Reconstruction

FOUR-DIMENSIONAL RECONSTRUCTION OF REGIONS EXHIBITING MULTIPLE PHASES OF PERIODIC MOTION

TECHNICAL FIELD

The present invention relates to systems and methods for four-dimensional reconstruction, and more particularly to systems and methods for building a four-dimensional reconstruction of a region exhibiting multiple phases of periodic motion.

BACKGROUND

As is known in the art, the process of image reconstruction includes several processes of rebuilding an image from a number of different image projections, the image projections being obtained, e.g., using computed tomography angiograms or other imaging modalities. Four-dimensional (4D) reconstruction involves the reconstruction of a 3D image as a function of a fourth parameter, e.g. time, the resulting 4D reconstruction permitting, e.g., the user to understand how the reconstructed 3D image behaves over time. The 4D reconstruction can serve as the basis for a prediction model, whereby information is provided as to behavior of the image over time. 4D reconstructions have been implemented in the field of medical imaging to visualize and model aneurysms in arteries of the human body, e.g., "CT Angiography with Electrocardiographically Gated Reconstruction for Visualizing Pulsation of Intercranial Aneurysms: Identification of Aneurysmal Protuberance Presumably Associated with Wall Thinning," M. Hayakawa et al., Am J Neroradiol, vol. 26, pgs. 1366-1369, June/July 2005, and Prediction of Impending Rupture in Aneurysms Using 4D-CTA: Histopathological Verification of a Real-Time Minimally Invasive Tool in Unruptured Aneurysms." Y. Kato et al. Minim. Invas. Neurosurg. Vol 47, pgs 131-35, 2004.

Techniques to obtain a 4D reconstruction have been disclosed by U.S. Pat. No. 6,643,392. This reference describes a technique whereby 2-D projections of an image are obtained at specific time intervals (or cardiac phases) over multiple cycles of periodic motion, each group of 2-D projections obtained at a particular cardiac phase serving as the basis for building a corresponding 3D reconstruction. Multiple 3D reconstructions are subsequently built, each 3D reconstruction corresponding to a particular time interval or cardiac phase.

Subsequently, two successive 3D reconstructions are used to derive a law of geometric/spatial deformation occurring therebetween, this process repeated for each pair of successive 3D reconstructions. Finally, each of the 2-D projections is applied to the derived laws of spatial deformation to arrive at the 4D reconstruction of the image.

The processes by which the 4D reconstruction is built suffer from some disadvantages, one being the large number of 2-D projections required for accurate rending of the 4D reconstruction. For example, it is expected that two hundred or more 2-D projections would be needed to accurately build each of the 3D reconstructions, and twenty or more 3D reconstructions are needed to derive an accurate 4D reconstruction, resulting in approximately four thousand 2-D projections needed. Furthermore, if image artifacts are present in one of the pair of 3D reconstructions used to derive the spatial deformation law, the 3D-3D registration process used to derive the spatial deformation laws could operate to map those artifacts into two of the spatial deformation laws (as the 3D reconstructions other than the beginning and end 3D reconstructions are used twice), resulting in the errors being transferred to the resulting 4D reconstruction. When the above mentioned method is used with fewer projections, e.g. ten projections per motion phase with a total of twenty phases, it is very likely that during the 3D-3D registration process artifacts would be mapped to define the spatial transformation instead of anatomical structures.

Accordingly, what is needed is an improved 4D reconstruction process requiring fewer 2-D projections and which provides less artifact transmission.

SUMMARY OF THE INVENTION

It may be desirable to provide a 4D reconstruction technique having improved imaging accuracy and which requires fewer 2-D projections.

This need may be met by a method and system in accordance with the independent claims.

A method in accordance with one embodiment of the invention includes building one or more 3D reconstructions using a set of 2-D projections. The method further includes deriving one or more 3D model segments from each of the one or more 3D reconstructions, wherein a plurality of 3D model segments are formed thereby, and wherein each of the one or more 3D model segments is derived from a single one of the one or more 3D model segments. The plurality of derived 3D model segments forms a 4D reconstruction of the region of interest.

A system in accordance with one embodiment of the present invention includes a 3D reconstruction model and a derivation model. The 3D reconstruction module is configured to build one or more 3D reconstructions using a set of 2-D projections. The derivation module is configured to derive one or more 3D model segments from each of the one or more 3D reconstructions, wherein a plurality of 3D model segments are formed thereby, and wherein each of the one or more 3D model segments is formed from a single one of the one or more 3D model segments. The pluralities of derived 3D model segments collectively form a 4D reconstruction of the region of interest.

The gist of one aspect of the invention may be seen as deriving a 3D model segment from a single 3D reconstruction, the single 3D reconstruction taking the form of either (i) a motion-phase specific 3D reconstruction formed from a subset of 2-D projections having substantially the same motion phase, or (ii) a common mean 3D reconstruction formed from a set of 2-D projections taken over a multitude of different motion phases. Derivation of a 3D model segment from a single 3D reconstruction provides benefits in that fewer 2-D projections are required to build the 4D reconstruction. Further advantageously, artifact transmission to the 4D reconstruction is reduced compared to the conventional approach in which two 3D reconstructions are used to generate a corresponding 3D model segment.

The following describes exemplary features and refinements of a method for building the 4D reconstruction in accordance with the invention, although these features and refinements will apply to the system as well.

In one embodiment, the aforementioned operation of building one or more 3D reconstructions using a set of 2-D projections includes the operations of: (i) identifying a plurality of subsets within the set of 2-D projections, each subset of the 2-D projections corresponding to a different motion phase (e.g., a different cardiac phase) of the region of interest, and (ii) building a 3D reconstruction for each subset of 2-D projections, wherein a collective plurality of 3D reconstructions are formed. Further specifically within this embodiment, the operation of deriving one or more 3D model segments includes deriving a 3D model segment from a single one of the plurality of 3-D reconstructions, whereby a plurality of 3D model segments are formed. This exemplary embodiment allows the formation of motion-phase specific 3D segments, the collection of which forms a 4D reconstruction in accordance with the present invention.

Further particularly within the aforementioned embodiment, the operation of deriving one or more 3D model segments includes tuning each of the plurality of 3D model segments towards a respective one of the plurality of the 2-D projection subsets. This feature results in improved rendering accuracy for each 3D model segment, resulting in an improved 4D reconstruction of the region of interest.

Further specifically with regard to the aforementioned embodiment, the method includes alignment operations, whereby a reference feature within the region of interest is selected for each of the 3D model segments, the reference feature identifying substantially the same feature in each of the 3D model segments. The reference feature may be selected from the group consisting of a center of mass of a predefined feature within the region of interest, a shape property of a predefined feature within of the region of interest, or a predefined reference location within the region of interest. The 4D reconstruction is subsequently built by implementing a sequence of the 3D model segments, whereby the reference feature in at least one of the 3D model segments defines an alignment point to which the reference feature in each of the remaining 3D model segments are mutually aligned. This process ensures mutual alignment between the respective 3D model segments, resulting in an accurate 4D reconstruction of the region of interest.

In a second exemplary embodiment of the invention, the aforementioned operation of building one or more 3D reconstructions using a set of 2-D projections includes the operation of building a mean 3D reconstruction for the set of 2-D projections. Further specifically to the second embodiment, the operation of deriving one or more 3D model segments includes deriving a mean 3D model from said mean 3D reconstruction, and dividing said mean 3D model into a plurality of 3D model segments. Further specifically within this second embodiment, the operation of building one or more 3D reconstructions using a set of 2-D projections includes identifying a plurality of subsets within the set of 2-D projections, each subset of the 2-D projections corresponding to a different motion phase of the region of interest, and the aforementioned operation of deriving one or more 3D model segments includes tuning each of the plurality of 3D model segments towards one or more of the 2-D projections. This exemplary embodiment allows the formation of motion-phase specific 3D segments, the collection of which forms a 4D reconstruction in accordance with the present invention. Furthermore, as each 3D model segment is derived from the same mean 3D reconstruction, the 3D model segments are inherently aligned.

Further specifically with regard to the second exemplary embodiment, each 2-D projection includes a time stamp indicating the relative position within a sequence of 2-D projections the particular 2-D projection was obtained. More specifically, the tuning operation includes tuning each of the plurality of 3D model segments towards a respective one of the plurality of the 2-D projection subsets, and subsequently tuning each of the 3D model segments towards a respective one of the 2-D projections. Performing an initial tuning process in which each 3D segment is tuned to a subset of corresponding to a particular motion phase provides enhanced segment imaging, and the subsequent tuning process in which each 3D model segment is tuned to a particular 2-D projection provides improved temporal accuracy of the 4D reconstruction.

The 4D reconstruction of the ROI may be rendered a fourth dimension of either motion phase or time, thereby providing a motion phase sequence, or a time-lapse sequence of the 3D model segments, respectively. 4D reconstruction of the ROI in terms of a motion phase sequence is useful to identify phase-dependent phenomena of the structure. Similarly, 4D reconstruction of the region of interest in terms of a time-lapse sequence facilitates determining time-dependent phenomena.

The 4D reconstruction may be configured to provide the 3D model segments in one particular sequence, although the rendering in the in other sequence may be desired. Accordingly, conversion between motion-phase and time-lapse sequences would be useful.

Conversion from a motion phase sequence to a time-lapse sequence can be accomplished by identifying, for each 3D model segment, a motion phase thereof, and the time stamp of a 2-D projection having substantially said motion phase. Next, the 3D model segments are positioned to occupy a position along a time stamp axis, their respective positions corresponding to the time stamp of the 2-D projection having substantially said motion phase as the selected 3D model segment.

Conversion from a time-lapse sequence to a motion phase sequence can be accomplished by identifying, for each 3D model segment, a time stamp thereof, and the motion phase of a 2-D projection having substantially that time stamp. Next each 3-D model segment is positioned to occupy a position along a motion phase axis, their respective positions corresponding to the motion phase of the 2-D projection having the substantially similar time stamp as the selected 3D model segment.

The operations of the foregoing methods and operations may be realized by a computer program, i.e. by software, or by using one or more special electronic optimization circuits, i.e. in hardware, or in hybrid/firmware form, i.e. by software components and hardware components. The computer program may be implemented as computer readable instruction code in any suitable programming language, such as, for example, JAVA, C++, and may be stored on a computer-readable medium (removable disk, volatile or non-volatile memory, embedded memory/processor, etc.), the instruction code operable to program a computer of other such programmable device to carry out the intended functions. The computer program may be available from a network, such as the WorldWideWeb, from which it may be downloaded.

These and other aspects of the present invention will become apparent from and elucidated with reference to the embodiment described hereinafter.

DETAILED DESCRIPTION OF SPECIFIC EMBODIMENTS

Figure 1:
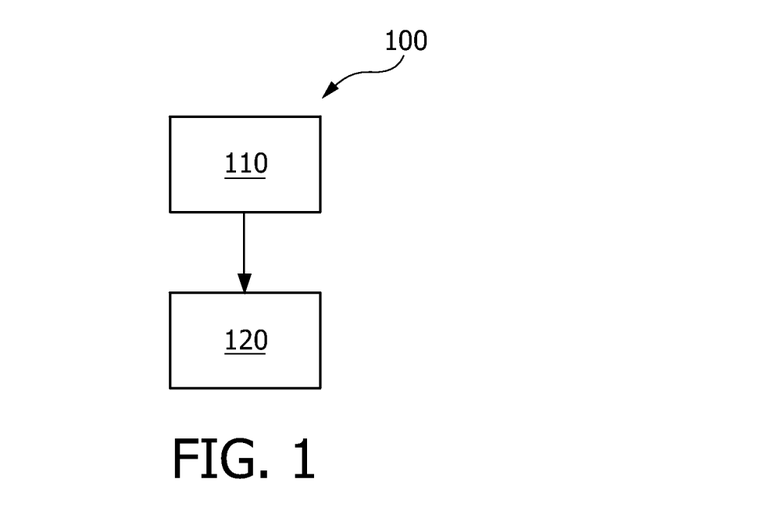
FIG. 1 illustrates an exemplary method for building a four-dimensional reconstruction of a region of interest exhibiting multiple phases of periodic motion in accordance with the present invention.

FIG. 1 illustrates an exemplary method for building a four-dimensional reconstruction of a region of interest exhibiting multiple phases of periodic motion in accordance with the present invention. The method 100 includes a first operation 110 of building one or more 3D reconstructions using a set of 2-D projections obtained for a region of interest over multiple phases of periodic motion. At 120, one or more 3D model segments are derived from each of the one or more 3D reconstructions, wherein a plurality of 3D model segments is formed thereby. Each of the one or more 3D model segments is derived from a single one of the one or more 3D reconstructions, and formation of a 4D reconstruction of the region of interest is achieved through the collective plurality of the 3D model segments.

As used herein, the terms "periodic motion phase," and "phases of periodic motion" ("motion phase" for brevity) refer to a particular state of the ROI within a range of periodic or cyclic motion the region experiences. For example, the ROI may include an organ such as the heart or lungs, in which case the motion may be cardiac or pulmonary/respiratory motions, the different phases of which being the "periodic motion phases" or "phases of periodic motion" referred to herein. Particularly with regard to cardiac motion, the terms "periodic motion phase" and "phases of periodic motion" includes those phases within a normal cycle of an ECG representing successive atrial depolarization/repolarization and ventricular depolarization/repolarization occurring with every heartbeat. As known in the art, these phases can be approximately associated with peaks and troughs of the ECG waveform labeled P, Q, R, S and T.

Further exemplary, the ROI may be an artery, or an aneurysm formed therein. In such embodiments, the "motion phases" of the ROI will be the different phases through which the artery or aneurysm moves, such motion perhaps determined by the cardiac phase of the heart supplying said artery. An exemplary embodiment of the invention presented below is described in terms of cardiac motion and phases thereof, although, as noted above the skilled person will understand that the invention is not limited thereto.

In a particular embodiment of the invention, the set of 2-D projections are gated radiographic/x-ray images or data corresponding thereto, the acquisition of which may be accomplished through a variety of means, e.g. an ECG-gated C-arm x-ray scanning system, as well as 2-D ultrasound. Other imaging techniques which may be used included rotational angiography, computed tomography angiography, and magnetic resonance angiography.

The set of 2-D projections acquired in process 110 may be in various forms, e.g., in electronic form, or in visually-rendered form. Furthermore, the set of 2-D projections acquired in 110 includes projections depicting the ROI in at least two different phases of motion. In a particular embodiment of the invention, the set of acquired 2-D projections is on the order of two hundred 2-D projections, although another number of projections (2, 3, 50, 100, 1000 or more) may be acquired during the operation of 110 in accordance with the present invention. Further particularly, the plurality of subsets of the 2-D projections generated in process 120 may be in a similar range, e.g. 2, 3, 50, 100, 1000 or more subsets. Each subset of 2-D projections may contain one projection of the ROI, or multiple projections of the ROI (e.g., 2, 3, 50, 100, 1000 or more projections). When multiple 2-D projections populate each subset, a single 2-D projection may be used which represents a weighted or un-weighted average of multiple projections included therein.

Optionally, each 2-D projection includes a time stamp indicating the relative position within a sequence of 2-D projections the particular 2-D projection was obtained. Those skilled in the art will appreciate various implementations may be used, for example a clock, counter, or other device or indicia operable to identify at what point in the collective sequence each 2-D projection is acquired in process 110.

In a first exemplary embodiment of the invention further illustrated in FIG. 2 below, a plurality of subsets of 2D projections are identified within the entire set of 2D projections, each subset containing 2-D projections of substantially the same motion phase. Subsequently, a 3D reconstruction is built for each subset of 2-D projections, and next, a 3D model segment is derived from a respective one of the 3D reconstructions. In this manner one 3D reconstruction is used to derive a corresponding 3D model segment. The plurality of the 3D model segments are assembled to form a motion phase sequence, although such a motion phase sequence can be translated into a time-lapse sequence, as will be further described below. Further optionally, each of the plurality of 3D model segments is tuned using the particular subset of 2D projections from which the 3D model segment was derived (i.e. via the corresponding 3D reconstruction), an exemplary process for which is described below.

In a second exemplary embodiment of the invention further illustrated in FIG. 3 below, the set of 2D projections are taken as a whole and a mean a 3D reconstruction is built therefrom. A mean 3D model is derived from the mean 3D reconstruction, and the mean 3D model divided into a plurality of 3D model segments. In this manner each of a plurality of 3D model segments is derived from a single one 3-D reconstruction. The plurality of the 3D model segments is assembled to form a 4D reconstruction. Further optionally, each of the plurality of 3D model segments is tuned using an identified subset of 2D projections, each subset including 2D projections of substantially the same phase motion in a manner similar to that described in the first exemplary embodiment.

From the foregoing, it can be seen that in contrast to the conventional registration approach in which multiple 3D reconstructions are used to obtain a 4D reconstruction, the present invention employs a single 3D reconstruction as the basis for deriving a corresponding 3D model segment, the collectively plurality of which form the 4D reconstruction. This approach requires significantly fewer 2-D projections compared with the conventional technique where a large number of 2-D projections are needed to provide the extensive number of the 3D reconstructions. Sufficient image quality can be achieved within a single rotational X-ray acquisition within about 7 seconds, 30 projections per seconds and an angular range of about 180°, for example.

Figure 2:
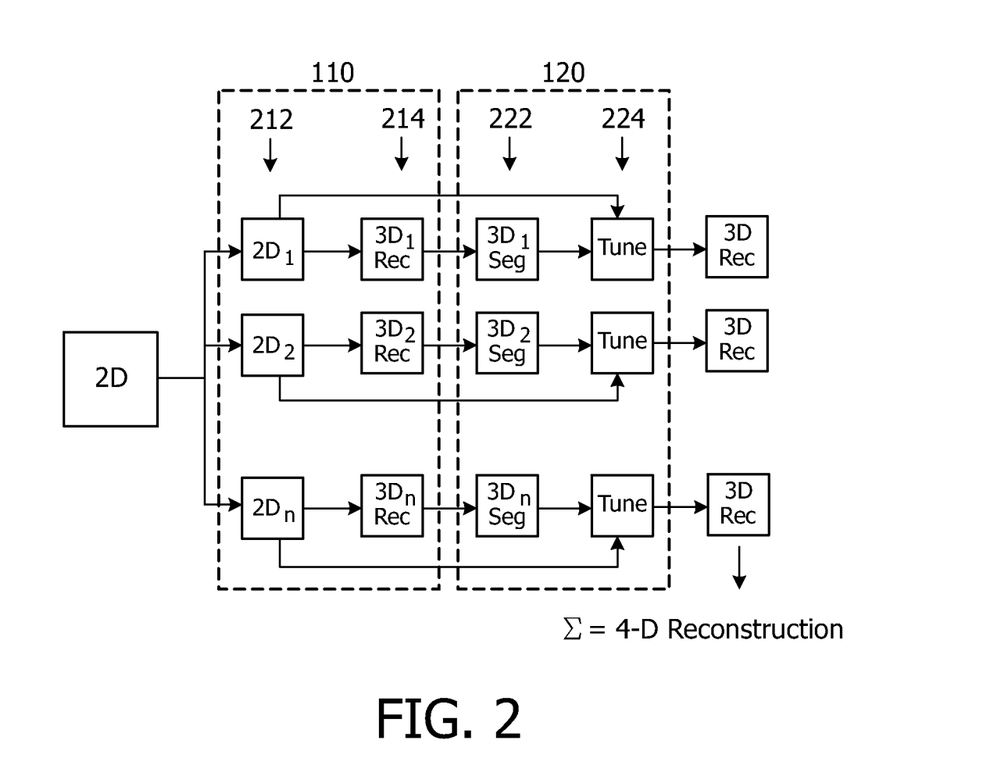
FIG. 2 illustrates exemplary processes of operations illustrated in FIG. 1 in accordance with a first exemplary embodiment of the invention.

FIG. 2 illustrates exemplary processes of 110 and 120 in accordance with a first exemplary embodiment of the invention. Exemplary processes of 110 include process 212, in which a plurality of subsets within the set of 2-D projections is identified, each subset of the 2-D projections corresponding to a different motion phase of the region of interest. At 214, a 3D reconstruction is built for each subset of 2-D projections, whereby a collective plurality of 3D reconstructions is formed. Exemplary processes of 120 include process 222 in which a 3D model segment is derived from a single one of the plurality of 3D reconstructions, whereby a plurality of 3D model segments is formed. A further process 224 includes tuning each of the plurality of 3D model segments using the particular subset of 2D projections from which the 3D model segment was derived (i.e. via the corresponding 3D reconstruction), an exemplary process for which is described below. The collective plurality of 3D model segments are aligned and assembled to form the 4D reconstruction of the ROI, an exemplary process for which is described below.

In a particular embodiment of the invention, the described motion phase of the region of interest is a cardiac phase of an aneurysm, the properties of which are to be modeled. In such an embodiment, process 212 includes performing an R-peak analysis to determine the particular cardiac phase of the 2D projection. Process 214 may be conducted by performing a gated reconstruction of each of the subsets of the 2-D x-ray images to generate a respective plurality of 3D reconstructions of the region of interest containing the aneurysm. Process 222 in which a 3D surface model segment is derived from each of the 3D reconstructions can be carried out using known processes, an example of which is described by M. R. Kaus, J. von Berg, J. Weese, W. Niessen, and V. Pekar. in "Automated Segmentation of the Left Ventricle in Cardiac MRI," Med. Img. Anal. 8 245-254, 2004.

Figure 3:
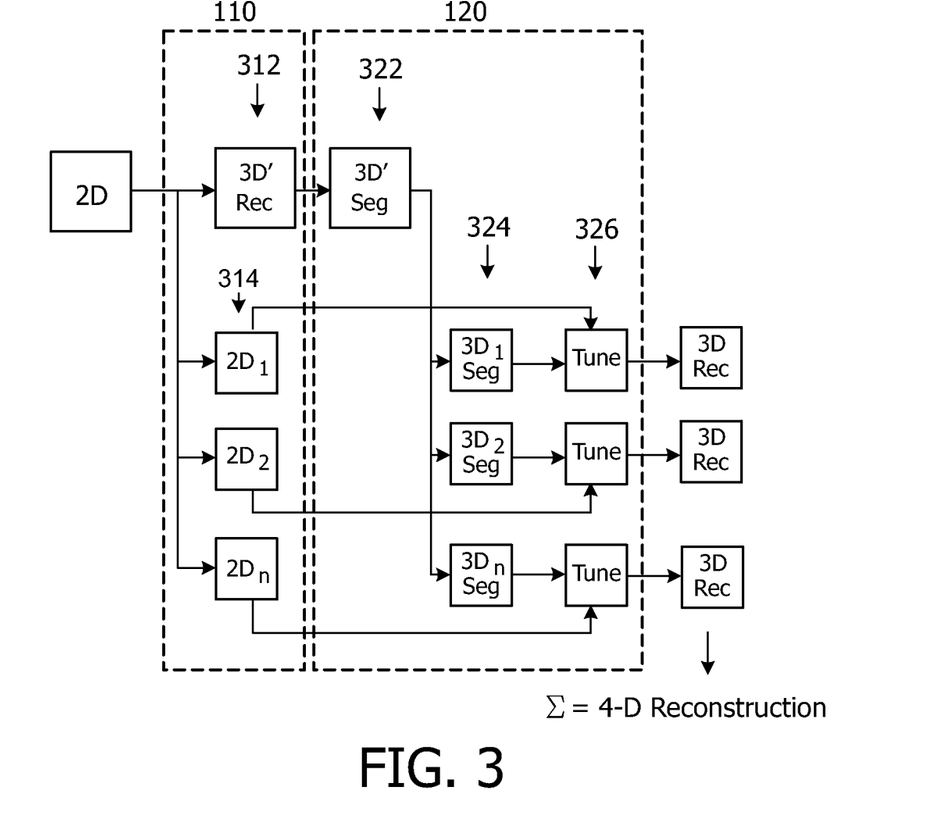
FIG. 3 illustrates exemplary processes of operations illustrated in FIG. 1 in accordance with a second exemplary embodiment of the invention.

FIG. 3 illustrates exemplary processes of 110 and 120 in accordance with a second exemplary embodiment of the invention. An exemplary process of 110 includes process 312, in which a set of 2D projections are taken as a whole, and a mean 3D reconstruction is built using substantially the entire set of 2-D projections. The term "mean 3D reconstruction" is intended to denote a collective 3D reconstruction which retains all of the 2D projection information therein. It is noted that in this particular embodiment, one gated reconstruction is performed over 2-D projections having multiple motion phases, whereas in the embodiment of FIG. 2, multiple gate reconstructions occur, each extending over a particular subset of 2-D projections having a particular motion phase. A further exemplary process of 110 includes process 314, in which a plurality of subsets within the set of 2-D projections is identified, each subset of the 2-D projections corresponding to a different motion phase of the region of interest. Gated reconstruction, however, is not performed over the subsets of 2-D projections in this embodiment; and the 2-D projection subsets are used instead for tuning, as will be described below.

Exemplary processes of 120 include 322, in which a mean 3D model is derived from the mean 3D reconstruction, the mean 3D segment also retaining all of the information provided by the collective plurality of 2D projection data. As a result, the mean 3D model will appear blurred, as the rendered image will include multiple motion phases of the ROI. At 324, the mean 3D model is divided into 3D model segments for formation of the 4D reconstruction.

In this manner each of a plurality of 3D model segments is derived from one (a mean) 3D reconstruction.

A further exemplary process of 120 includes process 326, in which each of the plurality of 3D model segments are tuned using a subset of 2D projections formed in process 314. The collective plurality of 3D model segments are assembled to form the 4D reconstruction of the ROI in terms of a motion phase sequence, although such a sequence can be translated into a time-lapse sequence, as will be further described below.

A particular embodiment of the invention is as described above, in which the described motion phase of the ROI is a cardiac phase of an aneurysm, the properties of which are to be modeled. In such an embodiment, process 312 may be conducted by performing a gated reconstruction of the acquired set of 2-D x-ray images to generate a mean 3D reconstruction of the region of interest containing the aneurysm, and process 314 carried out by performing an R-peak analysis to determine the particular cardiac phase of the 2D projection. Process 322 in which a mean 3D surface model segment is derived from the mean 3D reconstruction can be carried out using known processes, an example of which is described by M. R. Kaus, J. von Berg, J. Weese, W. Niessen, and V. Pekar. in "Automated Segmentation of the Left Ventricle in Cardiac MRI," Med. Img. Anal. 8 245-254, 2004.

Spatial division of the mean 3D model into a plurality of 3D model segments in process can be carried out by using known processes, for example using a subset of points within the mean 3D model. An exemplary number of segments into which the mean 3D model is divided may be 2, 3, 5, 50, 100, 1000 or more segments. In a particular embodiment, the number of 3D model segments corresponds to the number of 2-D projection subsets identified in process 314 above.

3D Model Segment Tuning Methodology

The method of the present invention may include tuning processes in order to more accurately render the 3D model segments that form the 4D reconstruction. Each 3D model segment may be tuned towards one or more 2D projection representative of a particular motion phase, towards a 2D projection having a particular time stamp of a, or a combination of both types of 2D projections in accordance with the present invention. In an exemplary embodiment of process 224, each of the resulting 3D model segments is tuned toward the subset of 2-D projections from which the 3D model segment was originally derived (i.e., via a corresponding 3-D reconstruction). This tuning process operates to correct for any mis-alignment in the motion phase that may occur when the 3D model segment is derived from it corresponding 3D reconstruction. In this manner, the motion phase of each 3D model segment is fine tuned before assembly into the 4D reconstruction. Optionally, the subset of 2D projections used for tuning the resultant 3D model segment may differ from the subset from which the corresponding 3D reconstruction is built. For example, the tuning version of the subset may include 2D projections having less variation in comparison with the reconstruction version, as less variation may facilitate more accurate tuning of the 3D model segment.

In a particular embodiment of the tuning process, one or more of the 2-D projections is used as reference, towards which a 3D model segment is tuned. A specific embodiment of this process would involve tuning each 3D model segment towards a subset of 2-D projections representative of that subset from which the segment's corresponding 3D reconstruction was built. The subset of 2-D projections is "representative" in that the subset employed for tuning may be different from the subset implemented for 3D reconstruction, as noted above. Tuning each 3D model segment to a plurality of 2-D projections having substantially the same motion phase provides enhanced imaging, as information from different 2-D images having substantially the same motion phase can be used to construct an accurate 3D model segment for the particular motion phase.

In another specific embodiment of the tuning process, each 3D model segment is tuned toward a respective one 2-D projection having a particular time stamp. Exemplary of such an embodiment, each 3D model segment is tuned to one 2-D projection, the tuned 3D model segment incorporating the time stamp of the 2-D projection towards which the 3D model segment is tuned. This tuning approach provides an accurate time lapse sequence of 3D model segments which is rendered by the 4D reconstruction. In such an approach, the tuning process includes adjusting the 3D model segment such that its forward projection achieves a sufficient degree of correlation with the measured 2D projection.

In still a further specific embodiment of tuning process, each 3D model segment is tuned initially towards a respective subset of 2-D projections which describes a particular motion phase, and subsequently towards a respective one 2-D projection having a particular time stamp. A combination of these tuning processes results in a 4D reconstruction model which enjoys the advantages of enhanced ROI imaging obtained from the tuning the 3D segments toward respective motion phases, and an accurate time-lapse rendering realized from tuning the 3D-segments toward respective time-stamps.

In the foregoing exemplary embodiments, tuning may be performed by regularized optimization (direct or iterative) of the model parameters using a 2D-3D registration process, an example of which is described by J. Weese, G. P. Penney, P. Desmedt, T. M. Buzug, D. L. G. Hill, and D. J. Hawkes, "Voxel-based 2-D/3D Registration of Fluoroscopy Images and CT Scans for Image-Guided Surgery," IEEE Trans. Inform. Technol. Biomed., vol. 1, pp. 284-293, December 1997. Furthermore, the tuning process may include adjusting the projection parameters, modeling parameters, or both parameter types. Projection parameters relate to the projection data of the 3D surface model segments, the adjustment for which may be made using shape sensitive filters may to enhance rendering of particular features within the ROI. Model parameters relate to the 3D surface model segment, and may be adjusted by providing modeling code operable to adjust mechanical or structural features of the 3D model segment, for example, inertia, surface shape or volume moments.

Alignment of 3D Model Segments

In the illustrated embodiment of FIG. 2, formation of the 4D reconstruction is obtained through assembling the plurality of 3D model surface segments into a collective sequence. In order to facilitate the assembly process, one or more reference features within the region of interest may be used as keys to which each of the 3D surface model segments are mutually aligned.

Figure 4:
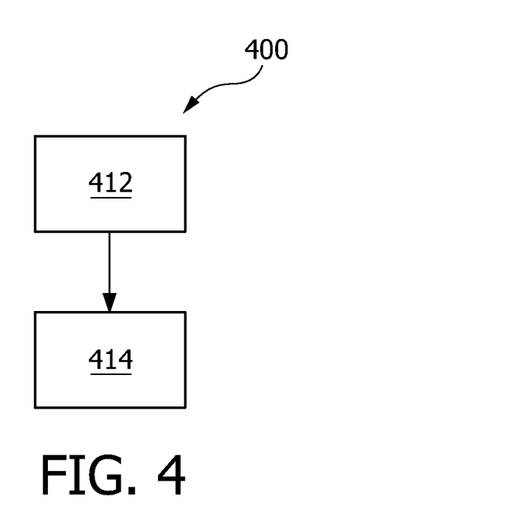
FIG. 4 illustrates an exemplary process for aligning multiple three-dimensional model segments derived in accordance with the present invention.

FIG. 4 illustrates an exemplary process 400 for aligning multiple three-dimensional model segments derived in accordance with the processes shown in FIG. 2 in accordance with the present invention. In this process, a reference feature is selected within the region of interest for each of the 3D model segments at 412, the reference feature identifying substantially the same feature in each of the 3D model segments. Assembly of the 4D reconstruction is generated at 414 by implementing a sequence of 3D model segments, whereby the reference feature in at least one of the 3D model segments defines an alignment point to which the reference feature in each of the remaining 3D model segments are mutually aligned.

The reference feature which serves as the alignment point may be a variety of features. In one example, the reference feature is a center or mass of a predefined feature within the region of interest, e.g., the center of mass of an aneurysm or other mass. In another embodiment, the reference feature is a surface property of a predefined feature within the ROI, e.g., the shape or curvature of the aneurysm within the ROI. In another embodiment, a predefined reference location within the ROI is used as the reference feature, for example, a point in the ROI which does not move substantially over time and/or with changes in cardiac phase of the aneurysm. In a specific embodiment, the reference feature is chosen on the basis that such feature can either be accurately tracked within the ROI over time and with changes in motion phase, or that the reference feature is not substantially displaced within the ROI over time and/or with changes in motion phase. The skilled person will appreciate that other reference features may be used alternatively or in addition to the aforementioned.

Moreover, while the aforementioned alignment process of FIG. 4 is described in terms of one reference feature, the skilled person will appreciate that an addition one or more additional reference features (2, 3, 5, 10, 100, or more reference features) may be added to provide further accuracy in aligning the 3D model segments, each reference feature in a particular 3D model segment providing an alignment point thereto for that reference feature in other 3D model segments.

With reference to the second exemplary embodiment of FIG. 3, all of the 3D model segments are derived from the same mean 3D reconstruction. As such, all of the 3D model segments are aligned to the same 3D volume, providing inherent mutual alignment between the 3D model segments. Translation of the 4D Reconstruction between Motion Phase and Time As noted, the 4D reconstruction may be provided (as electronic data, visually rendered, etc.) either in terms of a motion phase sequence, or as a time sequence. 4D reconstruction of the ROI in terms of a motion phase sequence is useful in that such a sequence is helpful to determine in which phase of motion a particular phenomenon occurs or to determine motion phase-dependent phenomenon. Such a sequence can be used to determine, for example, if it is likely that an aneurysm will rupture.

Providing a time lapse sequence of the ROI is also useful in identifying time-dependent phenomenon associated with the ROI. Other features, such as wall thinning may also be identified when viewing a time-lapse sequence of the ROI.

Figure 5A:
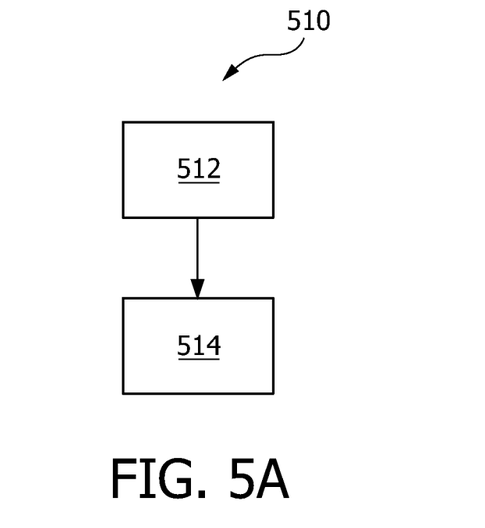
FIG. 5A illustrates an exemplary method of converting a time lapse sequence of 3D model segments to a motion phase sequence in accordance with the present invention.

Conversion between a time lapse sequence and a motion phase sequence may be performed by applying the appropriate 2-D projection(s) to each 3D model segment. FIG. 5A illustrates an exemplary method 510 of converting a time lapse sequence of 3D model segments to a motion phase sequence. Initially at 512, the time stamp of a 3D model segment is identified and the motion phase of the 2-D projection having substantially said time stamp also identified. At 514, the 3D model segment is mapped to occupy a position along a motion phase axis, said position corresponding to the motion phase of the 2-D projection having the substantially similar time stamp as the selected 3D model segment. This process is repeated for each of the 3D model segments, resulting in a motion phase sequence of 3D model segments. Time stamp information may be taken into account when ordering the 3D model segments; for example 3D model segments having substantially the same motion phase may be ordered left-to-right along an axis based upon the time stamps, the earliest 3D model segment being the left most and the latest 3D model segment occurring right most. Of course other orderings are possible as well.

Figure 5B:
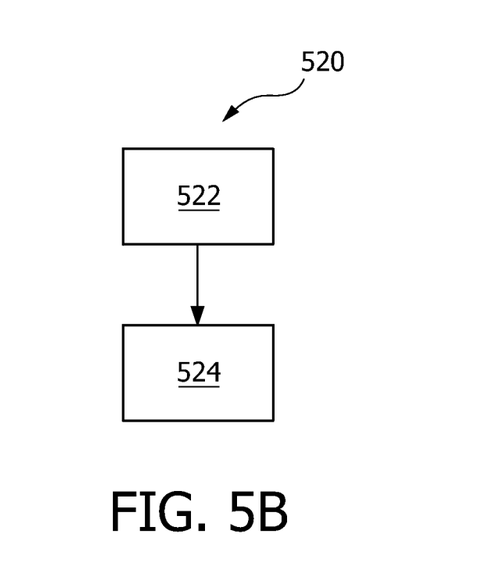
FIG. 5B illustrates an exemplary method of converting a motion phase sequence to a time lapse sequence in accordance with the present invention.

FIG. 5B illustrates an exemplary method 520 of converting a motion phase sequence to a time lapse sequence. Initially at 522, the motion phase of a 3D model segment is identified, and a 2-D projection have substantially the same time stamp is identified, the 2-D projection having a time stamp corresponding thereto. At 524, the 3D model segment is mapped to occupy a position along a time axis which corresponds to the time stamp of the 2-D projection. This process is repeated for each of the 3D model segments, resulting in a time sequence of 3D model segments.

Figure 6:
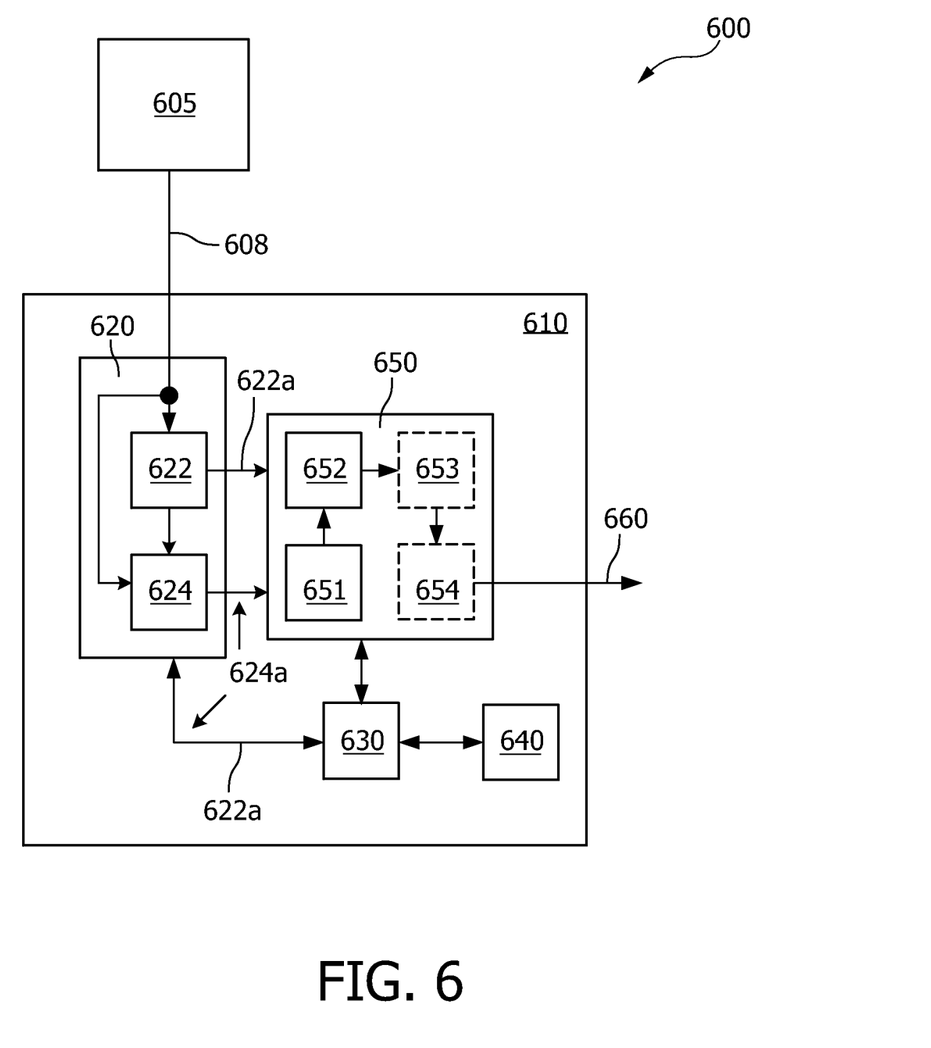
FIG. 6 illustrates an exemplary system for generating a four-dimensional reconstruction of a region of interest exhibiting multiple phases of motion in accordance with the present invention.

FIG. 6 illustrates an exemplary system 600 for building a four-dimensional reconstruction of a region of interest exhibiting multiple phases of motion in accordance with the present invention. Exemplary of a such a system, a ECG-gated C-arm x-ray scanning system 605 is operable to obtain gated 2D projections of a region of interest as the ROI exhibits a plurality of different phases of motion over time. Other scanning systems, such as multi-slice CT, ultrasound and the like may be used as well.

The acquired gated 2D projection data is supplied to the input 608 of a processing system 610, the processing system 610 realized in a particular embodiment as a computer. The processing system 610 further includes a 3D reconstruction module 620 for building one or more 3D reconstructions using a set of 2-D projections. The 3D reconstruction module 620 includes a recognition and sort module 622 operable to recognize differing motion phases of the received 2-D projections and to sort same into a plurality of different subsets, each subset containing 2-D projections of substantially the same motion phase, said information output at 622*a*. The 3D reconstruction module 620 further includes a gated 3D reconstruction module 624 operable to perform gated reconstruction of 2-D projection data. In one embodiment consistent with the method of FIG. 2, the gated reconstruction module 624 is operable to perform a gate reconstruction on each of the plurality of 2-D projection subsets provided by the recognition and sort module 622. In another embodiment consistent with the method of FIG. 3, the gated 3D reconstruction module 624 is operable to receive the set of 2D projection data from the input 610, and perform a gated reconstruction over substantially the entire set of received 2-D projection data. The gated reconstruction information is provided at 624*a*. Consistent with the embodiment of FIG. 3, data 624*a* corresponding to the subsets of 2D projection data is supplied from the 3D reconstruction module 620 to serve as reference data toward which the 3D segments are tuned in subsequent operations. Recognition functionality and gated 3D reconstruction(s) may be provided by executing instruction code running on an embedded processor 630 of the computer 600. Storage of the 2-D projections may be provided by volatile or non-volatile memory 640 coupled to said processor 630.

The processing system 610 further includes a derivation module 650 operable to derive 3D model segments from the one or more 3D reconstructions 624*a* provided. In a specific embodiment, the derivation module 650 includes a segment generator module 651 for forming 3D model segments from the 3D reconstruction(s) 624*a*. The derivation module 650 further includes a tuning module 652 operable to tune each of the 3D model segments toward one or more of the 2-D projections (e.g., stored in memory 640). In one embodiment, tuning module 652 is operable to tune a 3D model segment towards a respective one 2-D projection subset 622*a*, each 2-D projection subset exhibiting a different motion phase of the region of interest. In another embodiment, the tuning module 652 is operable to tune a 3D model segment to a respective one 2-D projection (e.g. accessed from memory 640 via processor 630), each 2-D projection exhibiting a different time stamp. Still further exemplary, the tuning module 652 is operable to tune a 3D model segment to initially a respective one 2-D projection subset to tune towards a particular motion phase, and subsequently to a respective one 2-D projection to tune towards a particular time stamp. Optionally, the derivation module 650 further includes an assembler module 653 for assembling the 3-D model segments either in a motion phase sequence or a time lapse sequence, the assembler module 653 performing the operations described in FIG. 4 to mutually align respective 3D segments derived in accordance with the method illustrated in FIG. 2. Such module may not be needed in an embodiment consistent with that of FIG. 3, and the module 653 can be omitted in such cases. Further optionally, the assembler module 654 further includes a converter operable to apply a conversion between time lapse and motion phase sequencing of the 3D model segments, as described in FIGS. 5A and 5B. In embodiments not employing this capability, the module 654 can be omitted.

It summary it may be seen as one aspect of the present invention that one aspect of the invention may be seen as deriving a 3D model segment from a single 3D reconstruction, the single 3D reconstruction taking the form of either (i) a motion-phase specific 3D reconstruction formed from a subset of 2-D projections having substantially the same motion phase, or (ii) a common mean 3D reconstruction formed from a set of 2-D projections taken over a multitude of different motion phases. Derivation of a 3D model segment from a single 3D reconstruction provides benefits in that fewer 2-D projections are required to build the 4D reconstruction. Further advantageously, artifact transmission to the 4D reconstruction is reduced compared to the conventional approach.

As readily appreciated by those skilled in the art, the described processes may be implemented in hardware, software, firmware or a combination of these implementations as appropriate. In addition, some or all of the described processes may be implemented as computer readable instruction code resident on a computer readable medium (removable disk, volatile or non-volatile memory, embedded processors, etc.), the instruction code operable to program a computer of other such programmable device to carry out the intended functions.

It should be noted that the term "comprising" does not exclude other features, and the definite article "a" or "an" does not exclude a plurality, except when indicated. It is to be further noted that elements described in association with different embodiments may be combined. It is also noted that reference signs in the claims shall not be construed as limiting the scope of the claims. The term "coupling" is used to indicate either a direct connection between two features, or an indirection connection, via an intervening structure, between two features. Operations illustrated in flow charts are not limited to the particular sequence shown, and later numbered operations may be performed currently with, or in advance of earlier number operations in accordance with the invention.

The foregoing description has been presented for purposes of illustration and description. It is not intended to be exhaustive or to limit the invention to the precise form disclosed, and obviously many modifications and variations are possible in light of the disclosed teaching. The described embodiments were chosen in order to best explain the principles of the invention and its practical application to thereby enable others skilled in the art to best utilize the invention in various embodiments and with various modifications as are suited to the particular use contemplated. It is intended that the scope of the invention be defined solely by the claims appended hereto.

What is claimed is:

1. A method for building a 4D reconstruction of a region of interest exhibiting multiple phases of periodic motion, the method comprising:
   (i) building, with a processor, a plurality of 3D reconstructions using a plurality of subsets of 2-D projections which are identified from a set of 2-D projections, wherein each of the plurality of subsets of the 2-D projections corresponds to a different motion phase of the region of interest and each of the 3D reconstructions corresponds to a different one of the plurality of subsets; and
   (ii) deriving, with the processor, one or more 3D model segments from each of said plurality of 3D reconstructions, wherein a plurality of 3D model segments are formed thereby, and wherein each of the one or more 3D model segments is derived from a single one of the plurality of 3D reconstructions, wherein, the plurality of derived 3D model segments forms a 4D reconstruction of the region of interest.

2. The method of claim 1, wherein (ii) further comprises tuning each of the plurality of 3-D model segments towards a respective one of the plurality of the 2-D projection subsets.

3. The method of claim 1, further comprising:
   selecting a reference feature within the region of interest for each of the 3D model segments, said reference feature identifying substantially the same feature in each of the 3D model segments, wherein the four-dimensional reconstruction is built by implementing a sequence of the 3D model segments, whereby said reference feature in at least one of the 3D model segments defines an alignment point to which the reference feature in each of the remaining 3D model segments are mutually aligned.

4. The method of claim 3, wherein the reference feature is selected from the group consisting of a center of mass of a predefined feature within the region of interest, a shape property of a predefined feature within of the region of interest, or a predefined reference location within the region of interest.

5. The method of claim 1, wherein (i) comprises building a mean 3D reconstruction for said set of 2-D projections, and wherein (ii) comprises: deriving a mean 3D model from said mean 3D reconstruction; and dividing said mean 3D model into a plurality of 3D model segments.

6. The method of claim 5, wherein (i) comprises identifying a plurality of subsets within the set of 2-D projections, each subset of the 2-D projections corresponding to a different motion phase of the region of interest; and wherein (ii) further comprises tuning each of the plurality of 3D model segments towards one or more of the 2-D projections.

7. The method of claim 6, wherein tuning comprises tuning each of the plurality of 3D model segments towards a respective one of the plurality of the 2-D projection subsets.

8. The method of claim 7, wherein each 2-D projection includes a time stamp indicating the relative position within a sequence of 2-D projections the particular 2-D projection was obtained, and wherein tuning further comprises tuning each of the plurality of 3D model segments towards a respective one of the 2-D projections.

9. The method of claim 1, wherein the plurality of 3-D model segments forms a motion phase sequence comprising a sequence of cardiac phases of the region of interest, the method further comprising: for each 3D model segment, identifying a motion phase thereof, and the time stamp of a 2-D projection having substantially said motion phase; and positioning said each 3D model segment to occupy a position along a time stamp axis, said position corresponding to the time stamp of the 2-D projection having substantially said motion phase as the selected 3D model segment.

10. The method of claim 1, wherein the plurality of derived 3D model segments forms a time lapse sequence, the method further comprising:
    for each 3D model segment, identifying a time stamp thereof, and the motion phase of a 2-D projection having substantially said time stamp; and
    positioning said each 3D model segment to occupy a position along a motion phase axis, said position corresponding to the motion phase of the 2-D projection having the substantially similar time stamp as the selected 3D model segment, wherein said motion phase comprises a cardic phase of said region of interest.

11. The method of claim 1, wherein the 2-D projections in a subset of the 2-D projections correspond to a same motion phase of the region of interest.

12. The method of claim 1, wherein the one or more 3D model segments are 3D surface model segments having a surface shape structural feature.

13. A system configured to build a four-dimensional reconstruction of a region of interest exhibiting multiple phases of motion, the system comprising:
    a processor that builds a plurality of 3D reconstructions using a plurality of subsets of 2-D projections of a set of 2-D projections, wherein each of the plurality of subsets of the 2-D projections corresponds to a different motion phase of the region of interest and that derives one or more 3D model segments from each of said plurality of 3D reconstructions, wherein each of the 3D reconstructions corresponds to a different one of the plurality of subsets, wherein a plurality of 3D model segments are formed thereby, and wherein each of the one or more 3D model segments is formed from a single one of the plurality of 3D reconstructions, wherein, the plurality of derived 3D model segments collectively forms a 4D reconstruction of the region of interest.

14. The system of claim 13, further comprising an ECG-gated C-arm x-ray scanning system.

15. The system of claim 13, wherein the 2-D projections in a subset of the 2-D projections correspond to a same motion phase of the region of interest.

16. The system of claim 13, wherein the one or more 3D model segments are 3D surface model segments having a surface shape structural feature.

17. A computer program product, resident on a non-transitory computer readable medium, for providing instruction code to build a 4D reconstruction of a region of interest which exhibits multiple phases of periodic motion, the computer program product comprising:
    instruction code to build plurality of 3D reconstructions using a plurality of subsets of 2-D projections of a set of 2-D projections, wherein each of the plurality of subsets of the 2-D projections corresponds to a different motion phase of the region of interest; and instruction code to derive one or more 3D model segments from each of said plurality of 3D reconstructions, wherein each of the 3D reconstructions corresponds to a different one of the plurality of subsets, wherein a plurality of 3D model segments are formed thereby, and wherein each of the one or more 3D model segments is derived from a single one of the plurality of 3D reconstructions, wherein, the plurality of derived 3D model segments forms a 4D reconstruction of the region of interest.

18. The computer program product of claim 17, wherein the 2-D projections in a subset of the 2-D projections correspond to a same motion phase of the region of interest.

19. The computer program product of claim 17, wherein the one or more 3D model segments are 3D surface model segments having a surface shape structural feature.

\* \* \* \* \*